United States Patent
Suen et al.

(10) Patent No.: US 9,227,920 B2
(45) Date of Patent: Jan. 5, 2016

(54) FRICTION MODIFIERS AND A METHOD OF MAKING THE SAME

(71) Applicant: Chevron Oronite Company LLC, San Ramon, CA (US)

(72) Inventors: Yat Fan Suen, Martinez, CA (US); Jennifer Elizabeth Newell, San Francisco, CA (US)

(73) Assignee: Chevron Oronite Company LLC, San Ramon, CA (US)

( * ) Notice: Subject to any disclaimer, the term of this patent is extended or adjusted under 35 U.S.C. 154(b) by 201 days.

(21) Appl. No.: 13/663,734

(22) Filed: Oct. 30, 2012

(65) Prior Publication Data

US 2014/0121140 A1    May 1, 2014

(51) Int. Cl.
| | |
|---|---|
| C10L 1/22 | (2006.01) |
| C10M 139/00 | (2006.01) |
| C07C 231/02 | (2006.01) |
| C10M 159/12 | (2006.01) |

(52) U.S. Cl.
CPC ............ *C07C 231/02* (2013.01); *C10M 139/00* (2013.01); *C10M 159/12* (2013.01); *C10M 2205/028* (2013.01); *C10M 2209/084* (2013.01); *C10M 2223/045* (2013.01); *C10M 2227/061* (2013.01); *C10N 2230/06* (2013.01); *C10N 2230/54* (2013.01); *C10N 2240/10* (2013.01); *C10N 2270/02* (2013.01)

(58) Field of Classification Search
CPC ......................... C10M 133/18; C10M 133/16
USPC ................................. 508/189, 194
See application file for complete search history.

(56) References Cited

U.S. PATENT DOCUMENTS

| | | | |
|---|---|---|---|
| 3,011,880 A | 12/1961 | Lioa et al. | |
| 4,231,883 A | 11/1980 | Malec | |
| 4,331,545 A | 5/1982 | Papay et al. | |
| 4,382,006 A | 5/1983 | Horodysky | |
| 4,389,322 A | 6/1983 | Horodysky | |
| 4,406,802 A | 9/1983 | Horodysky et al. | |
| 4,478,732 A * | 10/1984 | Horodysky et al. ........... | 508/190 |
| 6,245,725 B1 | 6/2001 | Tanaka et al. | |
| 6,803,350 B2 * | 10/2004 | Lantuejoul et al. ........... | 508/487 |
| 7,691,794 B2 | 4/2010 | Muir | |
| 8,803,352 B1 | 8/2014 | Koerber et al. | |
| 2005/0107623 A1 | 5/2005 | Fox et al. | |
| 2007/0155631 A1 | 7/2007 | Muir | |

FOREIGN PATENT DOCUMENTS

| | | |
|---|---|---|
| CN | 102702009 A | 10/2012 |
| EP | 393748 | 10/1990 |
| JP | 2005-320441 A | 11/2005 |
| WO | 2012/071185 A2 | 5/2012 |

OTHER PUBLICATIONS

Khanmohammadi, M. et al. "Quantitative Monitoring of the Amidation Reaction Between Coconut Oil and Diethanolamine by Attenuated Total Reflectance Fourier Transform Infrared Spectrometry", Journal of Surfactants and Detergents. Dec. 28, 2008, vol. 12, Issue 1; p. 38, scheme 1; p. 37 paragraph 3.

* cited by examiner

*Primary Examiner* — Prem C Singh
*Assistant Examiner* — Francis C Campanell
(74) *Attorney, Agent, or Firm* — Terrence M. Flaherty

(57) ABSTRACT

A method of preparing a lubricating oil additive composition comprising reacting (A) a nitrogen-containing reactant derived from reacting a first reaction product with a triglyceride, wherein the first reaction product is derived by reacting an alkanolamine and a base, wherein the nitrogen-containing reactant comprises three equivalents of a nitrogen-containing compound and one equivalent of glycerol, and wherein the nitrogen-containing reactant contains less than 10 mass percent of glycerol alkyl ester; (B) a source of boron; and (C) glycerol.

11 Claims, No Drawings

FRICTION MODIFIERS AND A METHOD OF MAKING THE SAME

FIELD OF THE INVENTION

This invention relates to new lubricating oil additives and lubricating oil compositions comprising the new lubricating oil additives. More specifically, it relates to passenger car engines and heavy duty diesel engines having lubricating oil compositions containing a friction reducing component comprising the reaction product of a multi-step synthesis that is co-borated with glycerol.

BACKGROUND OF THE INVENTION

In the realm of friction modifiers used in passenger car motor oils, there are many options. One of the many options available as an engine oil friction modifier is bis-ethoxy oleylamine which has been used for a number of years as a friction modifier.

Until recently, diesel engine oil formulators focused on the problem of maximizing the useful life of a lubricant and the engine it is used in. This has been done with the aid of wear inhibitors and antioxidants. Formulators had not spent too much time on tuning an engine oil's characteristics in order to maximize fuel economy.

A number of factors have contributed to the recent interest in improving diesel engine fuel economy. Global climate change legislation has slowly but steadily been limiting emissions from diesel engines. In addition, the price of crude oil skyrocketed in 2008. Suddenly fuel costs had superseded labor costs as the single largest expense of many truck fleets. Although the price of crude has dropped off significantly from where it peaked at $145/barrel in 2008, fuel economy is firmly established as an important issue for OEMs, diesel engine owners and diesel engine oil producers.

Addressing fuel economy in heavy duty diesel engines in a manner parallel to that used in passenger car engines has proven to not be the best strategy. Friction modifiers that have been used with success in passenger car engine oils show disappointing results in diesel engines. Reducing friction by reducing the viscosity of the oil has lead to wear issues. Obviously, a new approach is needed to tackle the problem of fuel economy in diesel engines.

New organic friction modifiers (OFMs) designed to function in both passenger car and heavy duty diesel engine oils have begun to emerge. Surprising benefits in friction reduction have been seen with a new class of mixed borate esters of bis-ethoxy alkylamines/amides. These benefits have been demonstrated through both bench and engine testing. A new method for synthesis of these additives from readily available starting materials has been developed.

Malec, U.S. Pat. No. 4,231,883 teaches the use of alkoxylated hydrocarbyl amines as friction modifiers.

Chien-Wei et al., U.S. Pat. No. 3,011,880 teaches the use of borate esters of bis alkoxylated hydrocarbyl amides as fuel additives to improve resistance to deposits and low temperature operation.

Colombo, EP393748 teaches the use of borate esters of mono and bis-ethoxylated alkyl amides as friction modifiers and anti corrosion agents in lubricants.

Papay et al., U.S. Pat. No. 4,331,545 teaches the use of borate esters of monoethoxylated hydrocarbyl amides as friction modifiers for both lubricants and fuels. Mixed borate esters with alkyl alcohols and polyhydric alcohols are described.

Horodysky, U.S. Pat. No. 4,382,006 teaches the use of borate esters of bis-ethoxylated alkyl amines as friction modifiers for lubricants. Example borate esters are mixed esters with butanol.

Horodysky, U.S. Pat. No. 4,389,322 teaches the use of borate esters of bis-ethoxylated alkyl amides as friction modifiers for lubricants. Example borate esters are mixed esters with butanol.

Horodysky et al., U.S. Pat. No. 4,406,802 teaches the use of mixed borate esters of compounds including bis-alkoxylated alkyl amines, bis-alkoxylated alkyl amides and alcohol hydroxyesters as friction modifiers in lubricants.

Horodysky et al., U.S. Pat. No. 4,478,732 teaches the use of mixed borate esters of compounds including bis-alkoxylated alkyl amines, bis-alkoxylated alkyl amides and alcohol hydroxyesters as friction modifiers in lubricants.

Yasushi, JP2005320441 teaches the use of a mixed borate ester of bis-ethoxylated alkyl amides and glycerol monoesters in low sulfur formulations as antiwear additives.

Fox et al., U.S. Patent Publication No. 20050107623 is directed to a method for reacting alkanolamine with ester in the presence of a metal silicate compound and, optionally, a catalyst, to produce a hydroxyalkyl amide composition with a decreased level of alkanolamine and residual catalyst.

None of the additives or methods of making the additives previously described utilize naturally occurring triglycerides as a starting material and address the problem of friction modification in a diesel engine oil with an alkyl alkanolamide that is co-borated with glycerol. Using triglycerides is both more cost effective and more environmentally friendly.

SUMMARY OF THE INVENTION

An embodiment of the present invention is directed to a method of preparing a lubricating oil additive composition comprising reacting (A) a nitrogen-containing reactant derived from reacting a first reaction product with a triglyceride, wherein the first reaction product is derived by reacting an alkanolamine and a base, wherein the nitrogen-containing reactant comprises three equivalents of a nitrogen-containing compound and one equivalent of glycerol, and wherein the nitrogen-containing reactant contains less than 10 mass percent of glycerol alkyl ester; (B) a source of boron; and (C) glycerol.

An embodiment of the present invention is directed to a lubricating oil additive composition comprising the reaction product of an (A) a nitrogen-containing reactant derived from reacting a first reaction product with a triglyceride, wherein the first reaction product is derived by reacting an alkanolamine and a base, wherein the nitrogen-containing reactant comprises three equivalents of a nitrogen-containing compound and one equivalent of glycerol, and wherein the nitrogen-containing reactant contains less than 10 mass percent of glycerol alkyl ester; (B) a source of boron, and (c) glycerol.

An embodiment of the present invention is directed to a lubricating oil composition comprising (A) a major amount of an oil of lubricating viscosity and (B) a lubricating oil additive composition comprising the reaction product of (i) a nitrogen-containing reactant derived from reacting a first reaction product with a triglyceride, wherein the first reaction product is derived by reacting an alkanolamine and a base, wherein the nitrogen-containing reactant comprises three equivalents of a nitrogen-containing compound and one equivalent of glycerol, and wherein the nitrogen-containing reactant contains less than 10 mass percent of glycerol alkyl ester; (ii) a source of boron, and (iii) glycerol.

An embodiment of the present invention is directed to a method for reducing friction in an internal combustion engine comprising lubricating said engine with a lubricating oil composition comprising the lubricating oil composition comprising (A) a major amount of an oil of lubricating viscosity and (B) a lubricating oil additive composition comprising the reaction product of (i) a nitrogen-containing reactant derived from reacting a first reaction product with a triglyceride, wherein the first reaction product is derived by reacting an alkanolamine and a base, wherein the nitrogen-containing reactant comprises three equivalents of a nitrogen-containing compound and one equivalent of glycerol, and wherein the nitrogen-containing reactant contains less than 10 mass percent of glycerol alkyl ester; (ii) a source of boron, and (iii) glycerol.

An embodiment of the present invention is directed to a lubricating oil additive concentrate comprising from about 90 wt. % to about 10 wt. % of an organic liquid diluent and from about 10 wt. % to about 90 wt. % of the lubricating oil additive composition comprising the reaction product of an (A) a nitrogen-containing reactant derived from reacting a first reaction product with a triglyceride, wherein the first reaction product is derived by reacting an alkanolamine and a base, wherein the nitrogen-containing reactant comprises three equivalents of a nitrogen-containing compound and one equivalent of glycerol, and wherein the nitrogen-containing reactant contains less than 10 mass percent of glycerol alkyl ester; (B) a source of boron, and (c) glycerol.

DETAILED DESCRIPTION OF THE INVENTION

While the invention is susceptible to various modifications and alternative forms, specific embodiments thereof and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DEFINITIONS

The following terms will be used throughout the specification and will have the following meanings unless otherwise indicated.

The term "amide" or "polyamide" refers to the reaction product of a carboxylic acid, carboxylate, anhydride of a carboxylic acid, or ester of a carboxylic acid and an amine, including polyamine.

The term "carboxylic acid component" refers to carboxylic acids, carboxylates, carboxylic anhydrides, and the esters of carboxylic acids.

Lubricating Oil Additive

In one embodiment, the lubricating oil additive is the reaction product of (1) a nitrogen-containing reactant that is derived from a multi-step synthesis process; (2) a source of boron, such as boric acid; and (3) glycerol.

Nitrogen-Containing Reactant

In one embodiment, the nitrogen-containing reactant is derived from a multi-step synthesis process.

The first step in the multi-step process comprises deprotonating an alkyl alkanolamine with a base to derive a first reaction product.

In one embodiment, the amine-containing reactant is an alkyl alkanolamine having the following structure:

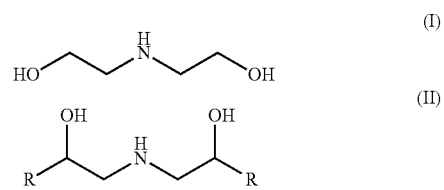

wherein R is hydrogen or has from about 1 to 2 carbon atoms.

Examples of alkanolamines include but are not limited to the following: diethanolamine and diisopropanolamine. Typically, the alkanolamine is diethanolamine.

In one embodiment, the base is a strong base. Preferably, the base is an alkoxide or carbonate (including bicarbonate), such as sodium hydroxide, potassium hydroxide, calcium hydroxide, sodium methoxide, sodium ethoxide, sodium propoxide, potassium methoxide, potassium ethoxide, potassium propoxide, potassium carbonate, sodium carbonate, sodium or potassium butoxide, sodium or potassium pentoxide, sodium or potassium hexanoate, cesium carbonate, calcium carbonate, strontium carbonate, barium carbonate, calcium bicarbonate and mixtures thereof. Preferably, the base is potassium hydroxide.

The first reaction product (i.e., deprotonated alkanolamine) is reacted with triglyceride. Typically the triglycerides have a saturated or unsaturated hydrocarbyl chain. Preferably, the triglycerides have mixtures of saturated and unsaturated hydrocarbyl chains and include, but are not limited to, triglycerides wherein the hydrocarbyl group comprises from about 6 to 20 carbon atoms or mixtures of 6 to 20 carbon atoms. More preferred, the triglyceride is coconut oil, which comprises approximately 66% medium chain triglycerides.

The products (i.e., nitrogen-containing reactant) of the reaction between triglyceride and the first reaction product (i.e., deprotonated alkanolamine), typically, comprise three equivalents of a nitrogen-containing compound and one equivalent of glycerol. The nitrogen-containing reactant contains a major part of alkanolamide and less than 10 mass percent of glycerol alkyl ester.

The nitrogen-containing compound is further reacted with a source of boron and additional glycerol.

Source of Boron Reactant

In one embodiment a source of boron such as boron trioxide or any of the various forms of boric acid—including meta-boric acid, ortho-boric acid, tetra-boric acid, alkyl borate—including mono-, di-, or tri-$C_1$-$C_6$ alkyl borate are used in the reaction. Preferably, boric acid is employed as the source of boron. Boric acid may be prepared by methods that are well known in the art. It may also be purchased from suppliers such as Aldrich and Fisher Scientific.

Glycerol

The glycerol component has the following structure:

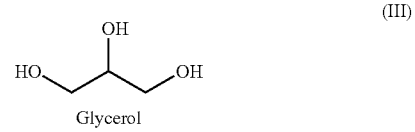

Glycerol

Method of Making the Lubricating Oil Additive Composition

The lubricating oil additive composition is prepared by charging a vessel with an alkanolamine, such as diethanolamine, and a base, such as potassium hydroxide. Water, which is a by-product of the reaction, is removed by distillation. A triglyceride, such as coconut oil, is then added to the vessel and mixed. The resulting product is nitrogen-containing and is, typically, an alkanolamide, such as a diethanolamide. A source of boron, such as boric acid, is then added to the vessel. The mixture is refluxed until the water has been substantially removed to drive the reaction to completion and then glycerol is added to the mixture.

In one embodiment, the glycerol is added to the vessel at the same time as the source of boron. The mixture is then refluxed for two hours.

Preferably the ratio of the nitrogen-containing reactant, the boric acid reactant and total glycerol is from about 1:0.33:0.33 to 1:3:3.

Additive Concentrates

In many instances, it may be advantageous to form concentrates of the oil soluble additive composition of the present invention within a carrier liquid. These additive concentrates provide a convenient method of handling, transporting, and ultimately blending into lubricant base oils to provide a finished lubricant. Generally, the oil soluble additive concentrates of the invention are not usable or suitable as finished lubricants on their own. Rather, the oil soluble additive concentrates are blended with lubricant base oil stocks to provide a finished lubricant. It is desired that the carrier liquid readily solubilizes the oil soluble additive of the invention and provides an oil additive concentrate that is readily soluble in the lubricant base oil stocks. In addition, it is desired that the carrier liquid not introduce any undesirable characteristics, including, for example, high volatility, high viscosity, and impurities such as heteroatoms, to the lubricant base oil stocks and thus, ultimately to the finished lubricant. The present invention therefore further provides an oil soluble additive concentrate composition comprising an inert carrier fluid and from 2.0% to 90% by weight, based on the total concentrate, of an oil soluble additive composition according to the invention. The inert carrier fluid may be a lubricating oil.

These concentrates usually contain from about 2.0% to about 90% by weight, preferably 10% to 50% by weight of the oil soluble additive composition of this invention and may contain, in addition, one or more other additives known in the art and described below. The remainder of the concentrate is the substantially inert carrier liquid.

Lubricating Oil Compositions

In one embodiment of the invention, the oil soluble additive composition of the present invention can be mixed with a base oil of lubricating viscosity to form a lubricating oil composition. The lubricating oil composition comprises a major amount of a base oil of lubricating viscosity and a minor amount of the oil soluble additive composition of the present invention described above.

The lubricating oil which may be used in this invention includes a wide variety of hydrocarbon oils, such as naphthenic bases, paraffin bases and mixed base oils as well as synthetic oils such as esters and the like. The lubricating oils which may be used in this invention also include oils from biomass such as plant and animal derived oils. The lubricating oils may be used individually or in combination and generally have viscosity which ranges from 7 to 3,300 cSt and usually from 20 to 2000 cSt at 40° C. Thus, the base oil can be a refined paraffin type base oil, a refined naphthenic base oil, or a synthetic hydrocarbon or non-hydrocarbon oil of lubricating viscosity. The base oil can also be a mixture of mineral and synthetic oils. Mineral oils for use as the base oil in this invention include, for example, paraffinic, naphthenic and other oils that are ordinarily used in lubricating oil compositions. Synthetic oils include, for example, both hydrocarbon synthetic oils and synthetic esters and mixtures thereof having the desired viscosity. Hydrocarbon synthetic oils may include, for example, oils prepared from the polymerization of ethylene, i.e., polyalphaolefin or PAO, or from hydrocarbon synthesis procedures using carbon monoxide and hydrogen gases such as in a Fisher-Tropsch process. Useful synthetic hydrocarbon oils include liquid polymers of alpha olefins having the proper viscosity. Likewise, alkyl benzenes of proper viscosity, such as didodecyl benzene, can be used. Useful synthetic esters include the esters of monocarboxylic acids and polycarboxylic acids, as well as mono-hydroxy alkanols and polyols. Typical examples are didodecyl adipate, pentaerythritol tetracaproate, di-2-ethylhexyl adipate, dilaurylsebacate, and the like. Complex esters prepared from mixtures of mono and dicarboxylic acids and mono and dihydroxy alkanols can also be used. Blends of mineral oils with synthetic oils are also useful.

The lubricating oil compositions containing the oil soluble additives of this invention can be prepared by admixing, by conventional techniques, the appropriate amount of the oil soluble additives of the invention with a lubricating oil. The selection of the particular base oil depends on the contemplated application of the lubricant and the presence of other additives. Generally, the amount of the oil soluble additive of the invention in the lubricating oil composition of the invention will vary from 0.05 to 15% by weight, preferably from 0.1 to 1% by weight, and more preferred from about 0.1 to 0.8% by weight based on the total weight of the lubricating oil composition.

The lubricating oil composition may be used in passenger car engines, heavy duty diesel engines, natural gas engines, tractor hydraulic fluids, marine diesel engines, railroad diesel engines and the like.

Additional Additives

If desired, other additives may be included in the lubricating oil and lubricating oil concentrate compositions of this invention. These additives include antioxidants or oxidation inhibitors, dispersants, rust inhibitors, anticorrosion agents and so forth. Also, anti-foam agents, stabilizers, anti-stain agents, tackiness agents, anti-chatter agents, dropping point improvers, anti-squawk agents, extreme pressure agents, odor control agents and the like may be included.

The following additive components are examples of some of the components that can be favorably employed in the lubricating oil compositions of the present invention. These examples of additional additives are provided to illustrate the present invention, but they are not intended to limit it:

Metal Detergents

Detergents which may be employed in the present invention include alkyl or alkenyl aromatic sulfonates, salycilates, calcium phenate, borated sulfonates, sulfurized or unsulfurized metal salts of multi-hydroxy alkyl or alkenyl aromatic compounds, alkyl or alkenyl hydroxy aromatic sulfonates, sulfurized or unsulfurized alkyl or alkenyl naphthenates, metal salts of alkanoic acids, metal salts of an alkyl or alkenyl multiacid, and chemical and physical mixtures thereof.

Anti-Wear Agents

As their name implies, these agents reduce wear of moving metallic parts. Examples of such agents include, but are not limited to, zinc dithiophosphates, carbamates, esters, and molybdenum complexes.

Rust Inhibitors (Anti-Rust Agents)

Anti-rust agents reduce corrosion on materials normally subject to corrosion. Examples of anti-rust agents include, but are not limited to, nonionic polyoxyethylene surface active agents such as polyoxyethylene lauryl ether, polyoxyethylene higher alcohol ether, polyoxyethylene nonyl phenyl ether, polyoxyethylene octyl phenyl ether, polyoxyethylene octyl stearyl ether, polyoxyethylene oleyl ether, polyoxyethylene sorbitol monostearate, polyoxyethylene sorbitol mono-oleate, and polyethylene glycol mono-oleate. Other compounds useful as anti-rust agents include, but are not limited to, stearic acid and other fatty acids, dicarboxylic acids, metal soaps, fatty acid amine salts, metal salts of heavy sulfonic acid, partial carboxylic acid ester of polyhydric alcohol, and phosphoric ester.

Demulsifiers

Demulsifiers are used to aid the separation of an emulsion. Examples of demulsifiers include, but are not limited to, block copolymers of polyethylene glycol and polypropylene glycol, polyethoxylated alkylphenols, polyesteramides, ethoxylated alkylphenol-formaldehyde resins, polyvinylalcohol derivatives and cationic or anionic polyelectrolytes. Mixtures of different types of polymers may also be used.

Friction Modifiers

Additional friction modifiers may be added to the lubricating oil of the present invention. Examples of friction modifiers include, but are not limited to, fatty alcohols, fatty acids, amines, ethoxylated amines, borated esters, other esters, phosphates, phosphites and phosphonates.

Multifunctional Additives

Additives with multiple properties such as anti-oxidant and anti-wear properties may also be added to the lubricating oil of the present invention. Examples of multifunctional additives include, but are not limited to, sulfurized oxymolybdenum dithiocarbamate, sulfurized oxymolybdenum organo phosphorodithioate, oxymolybdenum monoglyceride, oxymolybdenum diethylate amide, amine-molybdenum complexes, and sulfur-containing molybdenum complexes.

Viscosity Index Improvers

Viscosity index improvers, also known as viscosity modifiers, comprise a class of additives that improve the viscosity-temperature characteristics of the lubricating oil, making the oil's viscosity more stable as its temperature changes. Viscosity index improvers may be added to the lubricating oil composition of the present invention. Examples of viscosity index improvers include, but are not limited to, polymethacrylate type polymers, ethylene-propylene copolymers, styrene-isoprene copolymers, alkaline earth metal salts of phosphosulfurized polyisobutylene, hydrated styrene-isoprene copolymers, polyisobutylene, and dispersant type viscosity index improvers.

Pour Point Depressants

Pour point depressants are polymers that are designed to control wax crystal formation in lubricating oils resulting in lower pour point and improved low temperature flow performance. Examples of pour point depressants include, but are not limited to, polymethyl methacrylate, ethylene vinyl acetate copolymers, polyethylene polymers, and alkylated polystyrenes.

Foam Inhibitors

Foam inhibitors are used to reduce the foaming tendencies of the lubricating oil. Examples of foam inhibitors include, but are not limited to, alkyl methacrylate polymers, alkylacrylate copolymers, and polymeric organosiloxanes such as dimethylsiloxane polymers.

Metal Deactivators

Metal deactivators create a film on metal surfaces to prevent the metal from causing the oil to be oxidized. Examples of metal deactivators include, but are not limited to, disalicylidene propylenediamine, triazole derivatives, thiadiazole derivatives, bis-imidazole ethers, and mercaptobenzimidazoles.

Dispersants

Dispersants diffuse sludge, carbon, soot, oxidation products, and other deposit precursors to prevent them from coagulating resulting in reduced deposit formation, less oil oxidation, and less viscosity increase. Examples of dispersants include, but are not limited to, alkenyl succinimides, alkenyl succinimides modified with other organic compounds, alkenyl succinimides modified by post-treatment with ethylene carbonate or boric acid, alkali metal or mixed alkali metal, alkaline earth metal borates, dispersions of hydrated alkali metal borates, dispersions of alkaline-earth metal borates, polyamide ashless dispersants and the like or mixtures of such dispersants.

Anti-Oxidants

Anti-oxidants reduce the tendency of mineral oils to deteriorate by inhibiting the formation of oxidation products such as sludge and varnish-like deposits on the metal surfaces. Examples of anti-oxidants useful in the present invention include, but are not limited to, phenol type (phenolic) oxidation inhibitors, such as 4,4'-methylene-bis(2,6-di-tert-butylphenol), 4,4'-bis(2,6-di-tert-butylphenol), 4,4'-bis(2-methyl-6-tert-butylphenol), 2,2'-methylene-bis(4-methyl-6-tert-butylphenol), 4,4'-butylidene-bis(3-methyl-6-tert-butylphenol), 4,4'-isopropylidene-bis(2,6-di-tert-butylphenol), 2,2'-methylene-bis(4-methyl-6-nonylphenol), 2,2'-isobutylidene-bis(4,6-dimethylphenol), 2,2'-5-methylene-bis(4-methyl-6-cyclohexylphenol), 2,6-di-tert-butyl-4-methylphenol, 2,6-di-tert-butyl-4-ethylphenol, 2,4-dimethyl-6-tert-butyl-phenol, 2,6-di-tert-1-dimethylamino-p-cresol, 2,6-di-tert-4-(N,N'-dimethylaminomethylphenol), 4,4'-thiobis(2-methyl-6-tert-butylphenol), 2,2'-thiobis(4-methyl-6-tert-butylphenol), bis(3-methyl-4-hydroxy-5-tert-10-butylbenzyl)-sulfide, and bis(3,5-di-tert-butyl-4-hydroxybenzyl). Diphenylamine-type oxidation inhibitors include, but are not limited to, alkylated diphenylamine, phenyl-alpha-naphthylamine, and alkylated-alpha-naphthylamine. Other types of oxidation inhibitors include metal dithiocarbamate (e.g., zinc dithiocarbamate), and methylenebis(dibutyldithiocarbamate). Also included are molybdenum-containing anti-oxidants, such as molybdenum succinimide.

Applications

Lubricating oil compositions containing the oil soluble additive compositions disclosed herein are effective as either fluid and grease compositions for modifying the friction properties of the lubricating oil which may, when used as a crankcase lubricant, lead to improved mileage for the vehicle being lubricated with a lubricating oil of this invention.

The lubricating oil compositions of this invention may be used in natural gas engine oils, marine cylinder lubricants as in crosshead diesel engines, crankcase lubricants as in automobiles and railroads, lubricants for heavy machinery such as steel mills and the like, or as greases for bearings and the like. Whether the lubricant is fluid or solid will ordinarily depend on whether a thickening agent is present. Typical thickening agents include polyurea acetates, lithium stearate and the like.

The following examples are presented to illustrate specific embodiments of this invention and are not to be construed in any way as limiting the scope of the invention

EXAMPLES

It was discovered that two different methods could be employed to prepare a friction modifier. The first method requires that a certain amount of diethanol amine (approx 2.7-3 equivalents) are reacted with 1 equivalent of coconut oil triglyceride (1 eq) to form 3 eq of diethanol amide and 1 eq glycerol. Then, typically, from about 0 to about 2.66 equivalents of additional glycerol and from about 0.33 to about 3 equivalents of boric acid can be added to the reaction mixture and the co-boration procedure can be carried out.

Example 1

A flask was charged with 50.65 grams of coconut oil, 22.2 grams of diethanolamine and heated to 150° C. for 2 hours. The temperature was lowered to 110° C., then 13.5 grams of boric acid and 12.9 grams of glycerol were added to the flask. The total ratio of triglyceride, diethanolamine, added glycerol and added boric acid is 1.0:2.7:1.8:2.7 equivalents, respectively. The reaction mixture was heated at 110° C. for three hours. A dean stark trap was used to collect water.

Example 2

Diethanolamine (42.7 g) and KOH (4.49 g) were charged into a 500 mL insulated 4-neck RB flask with a stir rod, thermocouple, nitrogen gas flow and a Deane-Stark trap. Strong vacuum was applied as the reaction mixture was stirred at 120° C. for 50 minutes using a stir motor and mantle. A light nitrogen flow was pushed to remove the water more effectively. Temperature was then cooled down to 60° C. and 120 g of glycerol trioleate was added dropwise over a period of 2.5 hours. Infrared spectra confirmed that diethanolamide was the dominant product and contained a very minor amount of ester. Boric acid (25.2 g) and glycerol (24.9 g) were charged to the reaction flask and temperature was raise to 120° C. with strong vacuum and nitrogen blanket to distill off water. The product was a light brown viscous liquid. The product was tested in the Mazda Screener.

Comparative Example A

Co-boration of bis-ethoxy cocamide was carried out by heating bis-ethoxy cocamide, boric acid and glycerol in the same flask; and, water was distilled from the product. A number of different ratios of bis-ethoxy cocamide to glycerol to boric acid were synthesized. The product of bis-ethoxy cocamide co-boration at a 1:1:1 charge mole ratio (1:1:1 of boric acid and glycerol) was tested in the Mazda engine as the Comparative Example A. The average brake specific fuel consumption is −1.5%.

Alternatively, the glycerol can be added when the boric acid addition is made. This mixture is refluxed overnight. Toluene is removed under reduced pressure to obtain the product.

Example 3

21.37 grams of diethanolamine (0.20 mol, 3 equivalents) were charged to a round-bottom flask and stirred at room temperature. To that, 8.6 grams (0.04 mol, 20 mol %) of a 25% solution of NaOMe in MeOH were added to the round-bottom flask. The reaction mixture was heated to 60° C. with strong $N_2$ flow and kept under the same conditions for 30 minutes. 60 grams of glyceryl triolate (0.068 mol, 1 eq.) were charged into an addition funnel and were added to the round-bottom flask. The reaction was maintained for 30 minutes. The temperature was maintained with a strong $N_2$ flow. 12.45 grams of glycerol (0.14 mol, 2 eq) and 21.17 grams (0.20 mol, 3 eq) of trimethyl borate were charged to the round-bottom flask in portions. The temperature was raised to 70° C. with strong $N_2$ flow to distill the methanol byproduct. The reaction was held for two hours under the same conditions. The resulting product was tested and analyzed using infrared spectrum.

Mazda Screener

The lubricating oil additives prepared in Examples 1 and 3 and in Comparative Example A were evaluated for fuel economy properties in the Mazda Screener.

All formulated lubricating oil compositions contained identical amounts of additives, exclusive of a friction modifier, (the "baseline additive package") including dispersant, detergents, zinc dialkyldithiophosphate, antioxidant, polymethacrylate pour point depressant, and olefin copolymer viscosity index improver. Friction modifiers, of the invention and comparative examples, were added as a top treat to this baseline formulation of 0.5 wt %.

The fuel economy performance of lubricating oil compositions containing different organic friction modifiers was evaluated. A V-6 2.5 L engine was adjusted to run at a rotational speed of 1400 r/min and a temperature of about 107-120° C. Three high detergent oil flushes were first run through the engine for twenty minutes each. The engine was then operated for two hours with a lubricant which contained the baseline lubricant formulation without a friction modifier. After two hours, thirty grams of a lubricating oil containing the baseline additive package was top treated with 0.5 wt % of the friction modifier and was added to the engine through a specially adapted oil fill cap. The engine was allowed to stabilize for two hours.

The brake specific fuel consumption (BSFC) was evaluated by averaging the BSFC for a period of one hour prior to the addition of the top treated lubricating oil composition and averaging the BSFC for a period of two hours immediately following the addition of the top treated lubricating oil composition. Results are reported as the change in BSFC between the BSFC of the one hour before the addition of the top treated lubricating oil composition and the BSFC of the two hours after the addition of the top treated lubricating oil composition. Results are reported as an average of two runs. A more negative value corresponds to higher fuel economy benefit. The results of this evaluation are shown in the table below.

TABLE 1

| Brake Specific Fuel Consumption Lubricating Oil Composition | |
|---|---|
| Friction Modifier | Brake Specific Fuel Consumption (BSFC %) Treat Rate (0.5%) |
| Example 1 | −1.62 |
| Example 3 | −1.48 |
| Comparative Example A | −1.5% |

The lubricating oil composition formulated with the friction modifier of the invention (Examples 1 and 3) has comparable friction reduction as that of the lubricating oil composition formulated with diethanolamide derived from coconut oil. It is observed that even though the friction modifiers of Examples 1 and 3 are derived from "greener" methods (e.g., starting with coconut oil itself) the friction modifier is equally as effective with respect to brake specific fuel consumption, which correlates to the efficiency of an engine.

What is claimed is:
1. A method of preparing a lubricating oil additive composition comprising reacting
   A. a nitrogen-containing reactant derived from reacting a first reaction product with a triglyceride, wherein the

1. first reaction product is derived by reacting an alkanolamine and a base, wherein the nitrogen-containing reactant comprises three equivalents of a nitrogen-containing compound and one equivalent of glycerol, and wherein the nitrogen-containing reactant contains less than 10 mass percent of glycerol alkyl ester;
B. a source of boron; and
C. glycerol.

2. Original A lubricating oil additive composition comprising the reaction product of an
   (a) a nitrogen-containing reactant derived from reacting a first reaction product with a triglyceride, wherein the first reaction product is derived by reacting, an alkanolamine and a base, wherein the nitrogen-containing reactant comprises three equivalents of a nitrogen-containing compound and one equivalent of glycerol, and wherein the nitrogen-containing reactant contains less than 10 mass percent of glycerol alkyl ester;
   (b) a source of boron, and
   (c) glycerol.

3. The lubricating oil additive composition of claim 2 wherein the nitrogen-containing reactant is an alkanolamide.

4. The lubricating oil additive composition of claim 3 wherein the alkanolamide is diethanolamide.

5. The lubricating oil additive composition of claim 2 wherein the source of boron is boric acid.

6. A lubricating oil composition comprising
   A. major amount of an oil of lubricating viscosity and
   B. a lubricating oil additive composition comprising the reaction product of (i) a nitrogen-containing reactant derived from reacting a first reaction product with a triglyceride, wherein the first reaction product is derived by reacting an alkanolamine and a base, wherein the nitrogen-containing reactant comprises three equivalents of a nitrogen-containing compound and one equivalent of glycerol, and wherein the nitrogen-containing reactant contains less than 10 mass percent of glycerol alkyl ester; (ii) a source of boron, and (iii) glycerol.

7. The lubricating oil additive composition of claim 6 wherein the nitrogen-containing reactant is an alkanolamide.

8. The lubricating oil additive composition of claim 7 wherein the alkanolamide is diethanolamide.

9. The lubricating oil composition of claim 6 wherein the source of boron is boric acid.

10. A method for reducing friction in an internal combustion engine comprising lubricating said engine with a lubricating oil composition comprising the lubricating oil composition in claim 6.

11. A lubricating oil additive concentrate comprising from about 90 wt. to about 10 wt. of an organic liquid diluent and from about 10 wt. % to about 90 wt. % of the lubricating oil additive composition of claim 2.

* * * * *